(12) United States Patent
Trabzon et al.

(10) Patent No.: US 11,161,113 B2
(45) Date of Patent: Nov. 2, 2021

(54) MICROCHANNEL HAVING A SPIRAL GEOMETRY STRUCTURED WITH ASYMMETRICAL CURLS FOR CONTINUOUS SEPARATION OF CANCER CELLS FROM BLOOD AND ENRICHMENT THEREOF IN THE CIRCULATORY SYSTEM

(71) Applicant: ISTANBUL TEKNIK UNIVERSITESI, Istanbul (TR)

(72) Inventors: Levent Trabzon, Istanbul (TR); Samir Jaber, Istanbul (TR); Utku Mustafa Sonmez, Istanbul (TR)

(73) Assignee: ISTANBUL TEKNIK UNIVERSITESI, Istanbul (TR)

( * ) Notice: Subject to any disclaimer, the term of this patent is extended or adjusted under 35 U.S.C. 154(b) by 264 days.

(21) Appl. No.: 16/480,702

(22) PCT Filed: Mar. 16, 2018

(86) PCT No.: PCT/TR2018/050106
§ 371 (c)(1),
(2) Date: Jul. 25, 2019

(87) PCT Pub. No.: WO2019/004964
PCT Pub. Date: Jan. 3, 2019

(65) Prior Publication Data
US 2019/0388893 A1 Dec. 26, 2019

(30) Foreign Application Priority Data

Mar. 17, 2017 (TR) .................... 2017/04078

(51) Int. Cl.
| | | |
|---|---|---|
| *B01L 3/00* | (2006.01) | |
| *G01N 1/28* | (2006.01) | |
| *G01N 15/02* | (2006.01) | |

(52) U.S. Cl.
CPC .... *B01L 3/502761* (2013.01); *G01N 15/0255* (2013.01); *B01L 2200/0652* (2013.01); *B01L 2300/08* (2013.01); *B01L 2400/086* (2013.01)

(58) Field of Classification Search
CPC ....... B01L 3/502761; B01L 2200/0652; B01L 2300/08; B01L 2400/086; B01L 3/5027;
(Continued)

(56) References Cited

U.S. PATENT DOCUMENTS

2009/0014360 A1 1/2009 Toner et al.
2014/0248621 A1 9/2014 Collins
(Continued)

FOREIGN PATENT DOCUMENTS

CN 102162815 A 8/2011
GN 105462834 A 4/2016
(Continued)

*Primary Examiner* — Brian J. Sines
(74) *Attorney, Agent, or Firm* — Bayramoglu Law Offices LLC

(57) ABSTRACT

A microchannel (1) having a spiral geometry structured with asymmetrical curls (2) that enables separation of metastasis cancer cells rarely found in blood from the blood cells and enrichment thereof, which forces the particles or the cells to focus quicker and where high-quality particle focusing in a wider flow rate range can be performed.

1 Claim, 7 Drawing Sheets

(58) Field of Classification Search
CPC . B01L 3/502753; B01L 3/00; G01N 15/0255; G01N 1/28
See application file for complete search history.

(56) References Cited

U.S. PATENT DOCUMENTS

| | | | |
|---|---|---|---|
| 2015/0285808 A1* | 10/2015 | Nagrath | B01L 3/502761 |
| | | | 435/7.23 |
| 2016/0123857 A1* | 5/2016 | Kapur | G01N 15/1484 |
| | | | 435/2 |
| 2017/0292104 A1* | 10/2017 | Ebrahimi Warkiani | |
| | | | C12M 29/10 |
| 2018/0136210 A1* | 5/2018 | Khoo | B01L 3/502761 |
| 2019/0344273 A1* | 11/2019 | Bhagat | G01N 15/1056 |

FOREIGN PATENT DOCUMENTS

| | | | |
|---|---|---|---|
| WO | 2014046621 A1 | 3/2014 | |
| WO | 2015057159 A1 | 4/2015 | |

* cited by examiner

MICROCHANNEL HAVING A SPIRAL GEOMETRY STRUCTURED WITH ASYMMETRICAL CURLS FOR CONTINUOUS SEPARATION OF CANCER CELLS FROM BLOOD AND ENRICHMENT THEREOF IN THE CIRCULATORY SYSTEM

CROSS REFERENCE TO THE RELATED APPLICATIONS

This application is the national phase entry of International Application No. PCT/TR2018/050106, filed on Mar. 16, 2018, which claims priority from Turkish Patent Application 2017/04078, filed on Mar. 17, 2017, the entire contents of which are incorporated herein by reference.

TECHNICAL FIELD

The invention relates to a microchannel having a spiral geometry structured with asymmetrical curls that enables separation of metastasis cancer cells that are rare in blood from the blood cells and enrichment thereof.

More specifically, the invention relates to a microchannel having a spiral geometry structured with asymmetrical curls that forces the particles or the cells to focus quicker and where high-quality particle focusing in a wider flow rate range can be performed.

BACKGROUND

Thanks to the nanotechnology achieved today, important problems in many fields such as physics, chemistry, and medicine can be solved by nanometer sized structures. One example of such structures is microchannels. Inside these channels where microfluidic technology is used and that are especially used in medicine and having μm sized radius, tens of cells can be placed individually and the medium around them can be changed and the effects of such change can be inspected or the force they apply to their surroundings can be measured and calculated.

In this technique, various microchannel systems have been developed.

In the United States patent document with application No US2009014360A1 of the known state of the art, different methods and devices are mentioned which enable focusing of molecules in desired direction along with a moving fluid into the plurality of the flow streams or microchannels with known positions. The molecules can be conveyed to the channels inside one or more microchannels as desired by the internal force provided by the fluid passing through said flow streams or microchannels having a pumping part. Also, it is mentioned that the microchannels connected to said pumping part are curled at desired diameters in an asymmetrical geometry and therefore the molecules in the fluid can be directed within the scope of desired parameters.

In the international patent document with application No WO2014046621A1 of the current state of the art, a sloped and continuous microfluidics device having one input is mentioned. In said document, it is mentioned that this microchannel can be configured as straight and curled or as a spiral.

In the Chinese patent document with application No CN105462834A, a microfluidic chip designed in spiral geometry with an input and output at its ends, manufactured to catch the tumor cells is mentioned.

However, in the microchannel systems comprised in the known state of the art, the cells must catch a certain flow rate and passed through a longer distance inside the channel in order to have a good focus. In this case, the cells with low strength against external mechanical effects cannot be used in microchannel systems due to the negative effects of the shear stress created by high flow rates. Moreover, the reliability of laboratory studies performed on cells obtained by separation through microchannels becomes suspected since the physiologic properties of the cells along with the vitality are changed by the external mechanical effects such as shear stresses.

In order to overcome the problems mentioned above, there exists a need for developing a microchannel having a spiral geometry structured with asymmetrical curls.

SUMMARY

The object of the invention is to embody a microchannel having spiral geometry, structured with asymmetrical curls where high quality particle focusing in a wide flow rate range is performed.

Another object of the invention is to embody a microchannel having a spiral geometry structured with asymmetrical curls that forces particles or cells to focus quicker.

Another object of the invention is to realize a microchannel having a spiral geometry structured with asymmetrical curls where the cells with low resistance against mechanical effects can be gathered inside the microchannel without being damaged.

Another object of the invention is to realize a microchannel having a spiral geometry structured with asymmetrical curls that shortens the diagnosis time.

The present cell mixture is pumped into the single entry point along with a fluid into the microchannel having spiral geometry (sunflower) structured with asymmetrical curls. While this cell-carrying fluid is circulating inside the microchannel having spiral geometry structured with asymmetrical curls, the deformable cells having different size and densities go to different points inside the channel due to resistance and drag forces created by the geometry of the microchannel. The cell groups formed after this process are taken to different exits at the end of the channel and they can be collected from these exits for examination. Thanks to the geometrical advantages of the microchannel of the invention, it does not require a membrane that can filter cells or external forces such as electrical, magnetic and acoustical forces and therefore the separation techniques can be performed passively.

BRIEF DESCRIPTION OF THE DRAWINGS

A microchannel having a spiral geometry structured with asymmetrical curls embodied to achieve the objects of the invention and experiment results are shown in figures.

In the drawings.

DETAILED DESCRIPTION OF THE EMBODIMENTS

Figure 1:
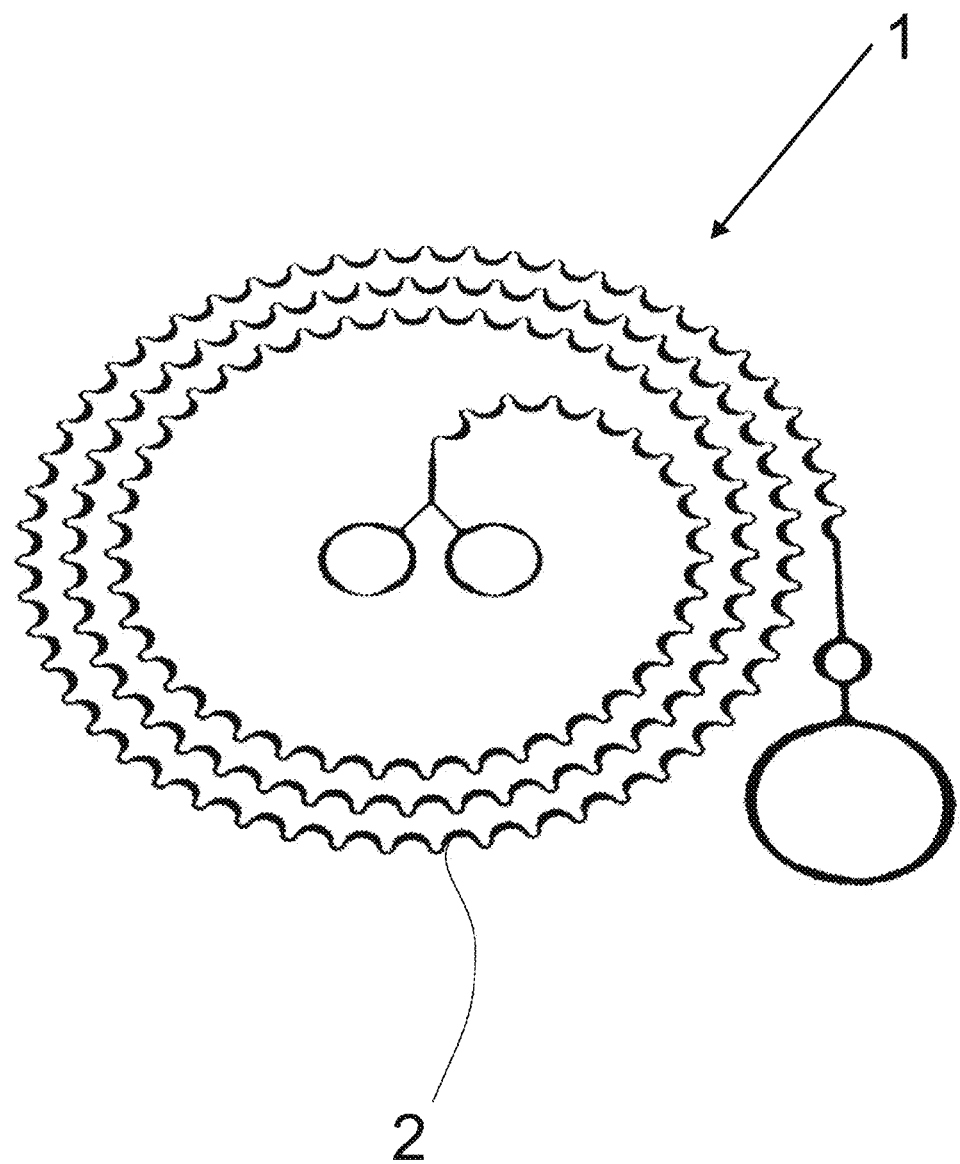
FIG. 1 is a view of the microchannel having a spiral geometry structured with asymmetrical curls.
Figure 2:
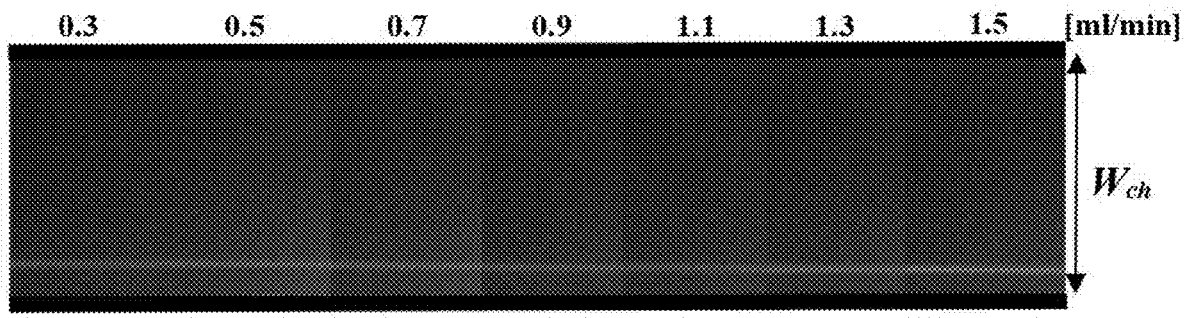
FIG. 2 is a fluorescent microscope view of the particle focus of the microchannel of the invention at variable flow rate between 0.3 ml/min and 1.5 ml/min.
Figure 3:
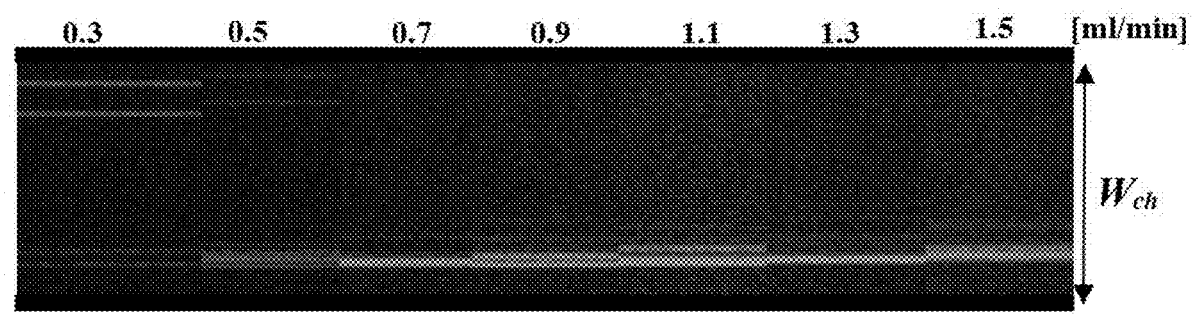
FIG. 3 is a fluorescent microscope view of the particle focus of the asymmetrical microchannel at variable flow rate between 0.3 ml/min and 1.5 ml/min.
Figure 4:
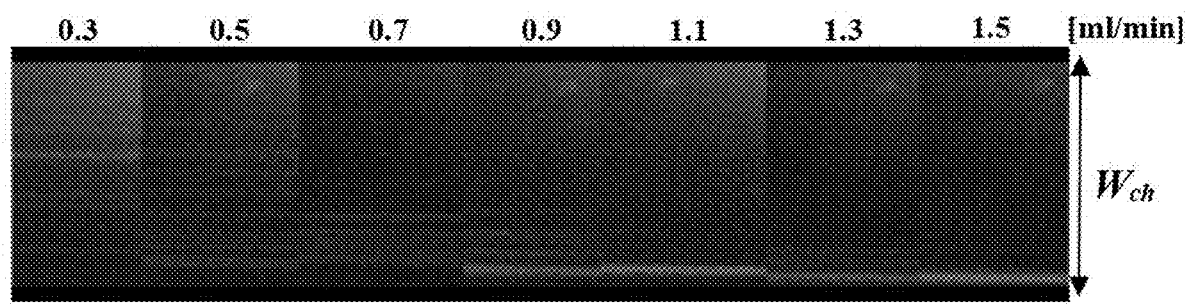
FIG. 4 is a fluorescent microscope view of the particle focus of the spiral microchannel at variable flow rate between 0.3 ml/min and 1.5 ml/min.
Figure 5:
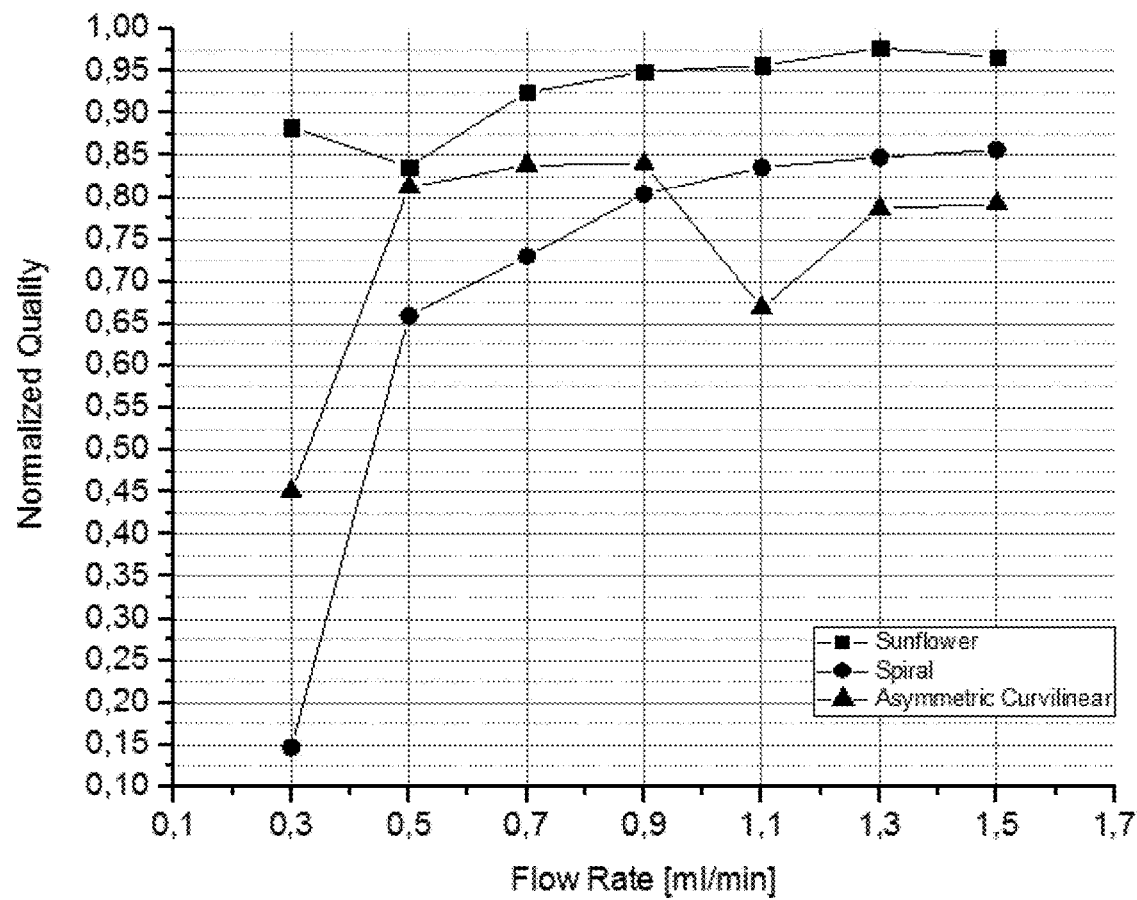
FIG. 5 is a graphic that quantitatively compares the quality of the particle focus obtained in the channels.

The invention is a microchannel (1);

comprising asymmetrical curls (2) and having a spiral geometry.

When applied in clinic and biology fields, microfluidics enable improved diagnosis of the cancer cells in the blood circulation by cell separation method. However, properties such as process efficiency, process speed and working precision substantially differ between microfluidic systems. While some systems require a membrane that can filter cells for cell separation, other systems require external forces such as electrical, magnetic and acoustic forces. Such systems bring along problems such as high costs, process and production complexity and undesired effects on cell vitality.

Passive separation techniques (general name of the techniques performing cell separation without any external forces) including the microchannel (1) of the invention are not developed enough to be used in practice due to their low efficiencies, relatively low process speeds and being only used at optimum working points.

When compared to conventional laboratory and clinical processes, the microchannel (1) (sunflower) having a spiral geometry structured with asymmetrical curls (2) can be seen as more compact, wider range and a more suitable structure in terms of time and cost. While other microfludic systems have limitations such as difficulty of application of production and working principles outside the laboratory environment, requiring external forces, requiring long process times and damaging the cells, a microchannel (1) having a spiral geometry structured with asymmetrical curls (2) overcomes these limitations. Since it is a structure that continuously separates the cells by the effect of hydrodynamic forces formed by the flow as opposed to active separation procedures, it can process more sample faster and shortens the diagnosis process.

The microchannel (1) having a spiral geometry structured with asymmetrical curls (2) can separate the cells independent of the form, type and electrical/magnetic properties of the cells. This microchannel (1) has a structure not containing any membrane and that does not require external forces. Thus, this system does not affect cell vitality.

In this way, rare cells or particles in a mixture can be separated and stored for future laboratory examinations. As opposed to the previous techniques, it provides ability to manipulate cell position continuously and with high precision at a substantially wide flow rate range. Moreover, due to the effective hydrodynamic forces formed by the special configuration of the geometry of this microchannel (1), it is a structure that can provide early focusing of the cells in a short time and at a short distance.

In the present systems, for a good focusing of the cells, the cells must catch a certain flow rate and passed through a long distance. However, the developed microchannel (1) overcomes these shortcomings. As this microchannel (1) can be used in cleaning of water contaminated by biological factors and in separation of particles or cells inside the samples collected at crime scenes that can serve as evidence, it can also contribute to the early diagnosis of the cancer through a technique named liquid biopsy.

In the microchannel (1), it is facilitated that the cancer cells leak into the blood line through metastasis long before primer cancer tissue can be diagnosed. Cancer cells that are at a very low rate inside the blood before the symptoms of the disease start can be separated to cells by processing a blood sample inside the microchannel (1) and the cancer cells can be identified. This facilitates the treatment of the disease through early diagnosis and eliminates financial and emotional difficulties that may emerge during the treatment at further stages of the disease.

Besides, the separated cancer cells can be collected from the system without being damaged which is not possible in many systems and can be sent to the related cell laboratories for further examinations. Thus, the type, location and size of the primer cancer can be identified and more effective treatments specific to the patient can be developed. These advantages are very important for the people in need, because the microchannel (1) provides an effective, highly efficient, cheap, small, mobile cancer diagnosis system when integrated with a peristaltic micropump.

One of the most important positive aspects of the microchannel (1) developed for particle separation and enrichment is that it can obtain high quality particle focusing at a very wide flow rate range. In order to test what improvements said property of the structure provides when compared to only spiral microchannel and only curved microchannel systems, different systems are produced at different sizes and tested at a wide flow rate range.

In the experiments conducted with polystyrene particles having 9.9 μm diameter which is the size of a typical mammalian cell, it is observed that particle focusing does not occur before 0.7 ml/min flow rate in other systems and particles are focused in a focal line between all flow rate ranges inside the developed microchannel (1) having a spiral geometry structured with asymmetrical curls (2). Moreover, even the focus is formed, it is observed that the particle focus occurs at a lower quality in other systems with respect to the quality of the particle focus of the microchannel (1) having a spiral geometry structured with asymmetrical curls (2). (FIG. 2, FIG. 3, FIG. 4 and FIG. 5) Conducted quantitative comparisons show that there is an improvement in focus quality and therefore in particle separation and enrichment potential up to 487% at low flow rates and up to 14% at optimum focusing flow rates.

These obtained results show that the particles can be focused better in the developed microchannel (1) when compared to other two systems and focus formation at low flow rates which cannot be observed in other systems can be observed. Thus, with the current geometry, not only fast focusing is realized, also an unexpected result is achieved and focus formation at low flow rates is observed.

The microchannel (1) having a spiral geometry structured with asymmetrical curls (2) exhibits a better particle focusing property whit respect to the spiral and curved microchannel systems. When it is not possible to adjust the working flow rate to the optimum value of the system (mostly, such systems do not work alone, they are connected to other systems in their inputs and outputs. When these systems need to run at another flow rate, the system is expected to adapt and tolerate the change in the flow rate) or it is not technically possible to precisely keep the desired flow rate at a certain value, this seems like the only solution.

Figure 6:
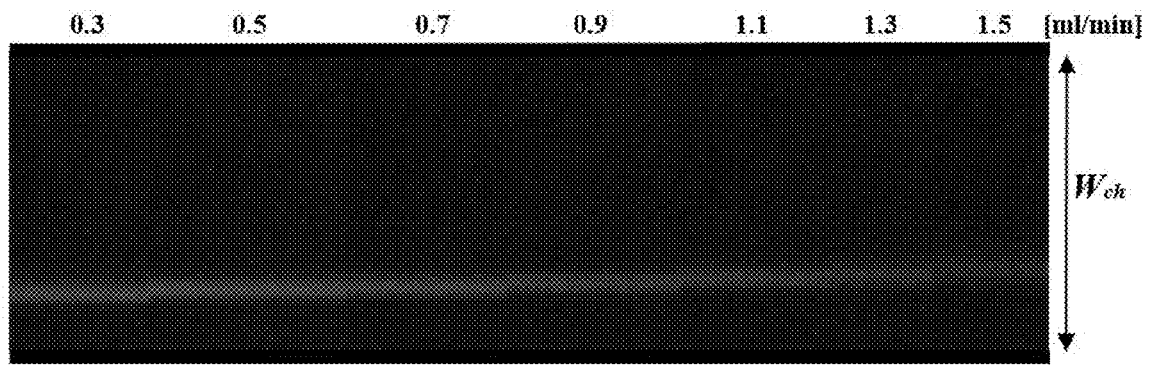
FIG. 6 is a microscope view of the focus lines of the microchannel having 50 μm height.
Figure 7:
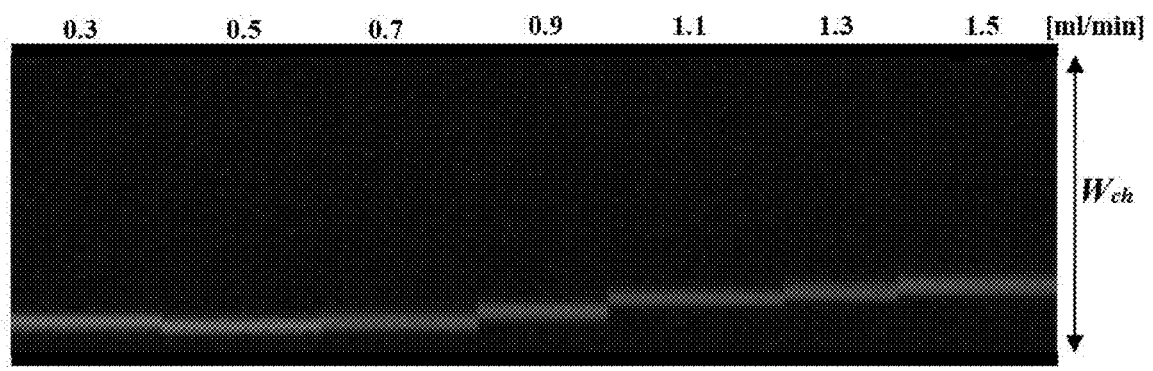
FIG. 7 is a microscope view of the focus lines of the microchannel having 60 μm height.
Figure 8:
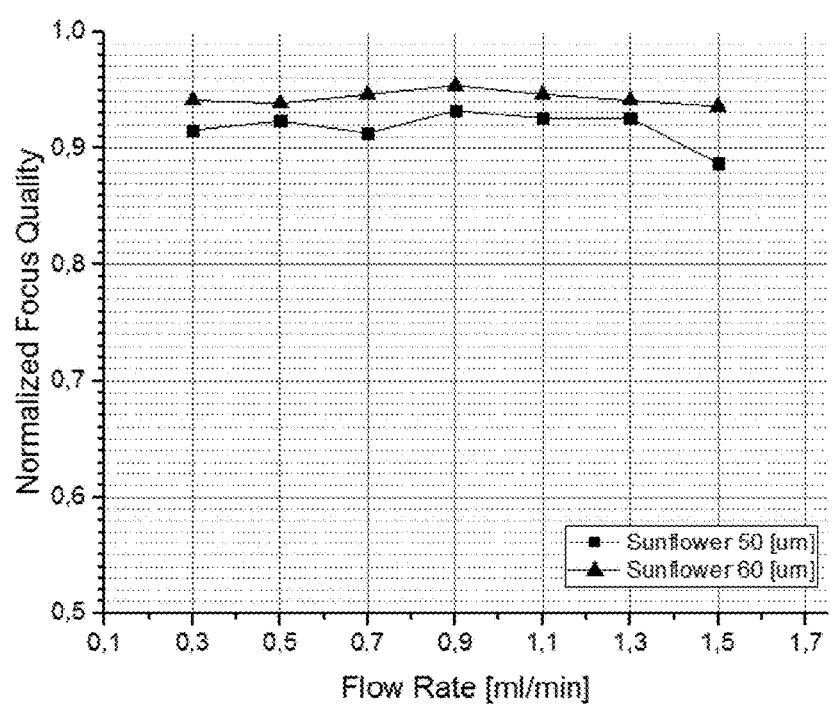
FIG. 8 is the graphic of the results obtained from the output of the microchannel having 50 μm and 60 μm heights.

The developed microchannel (1) is tested by using HL60 cancer cells and successful results are obtained. In the experiments with the microchannel (1) having spiral geometry structured with asymmetrical curls (2), high quality focal lines of the HL-60 cells obtained at a wide flow rate range can be observed at the results obtained from the output of the microchannel (1) having 50 μm and 60 μm heights. (FIG. 6, FIG. 7 and FIG. 8).

Figure 9:
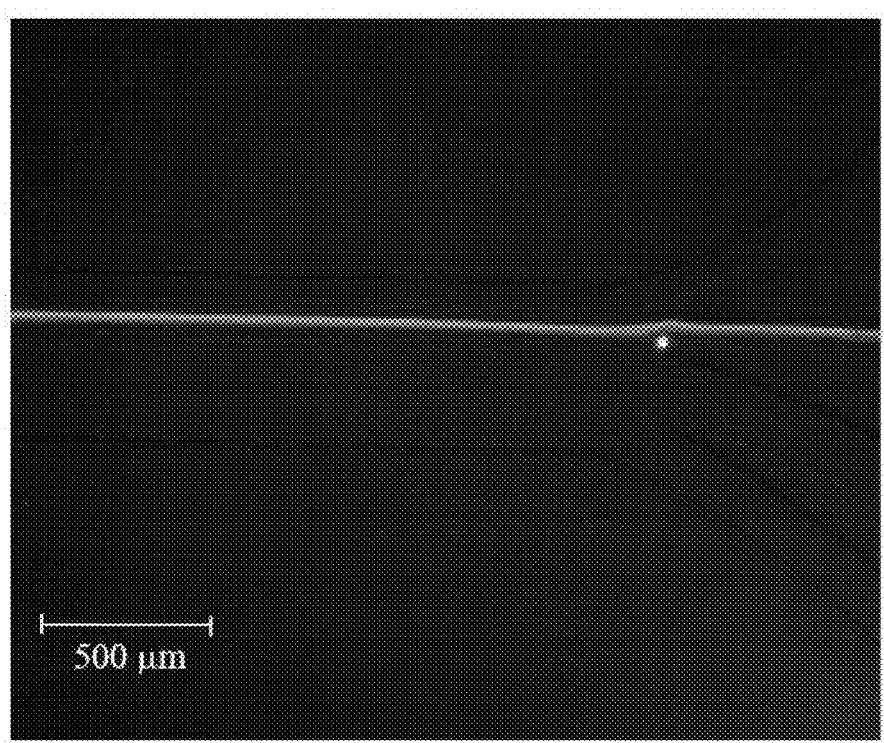
FIG. 9 is the microscope view of the particles at low flow rate while being collected at the output close to the wall in the microchannel.
Figure 10:
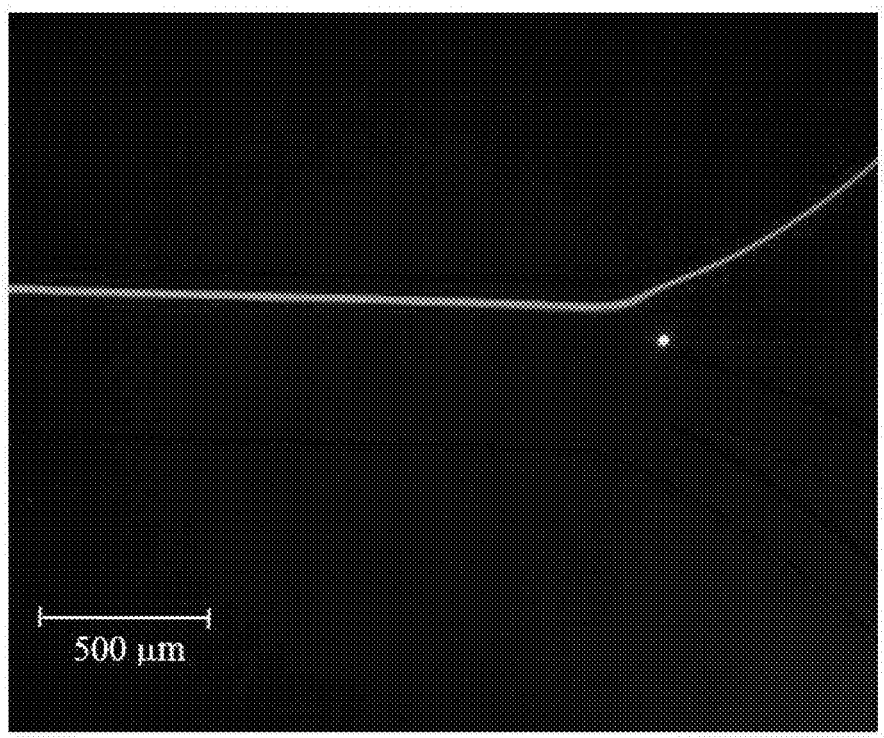
FIG. 10 is the microscope view of the particles at high flow rate while being collected from the other output close to the center of the microchannel.

In the light of these experiments, in order to exhibit the advantages of focusing particles or cells inside the channel at desired locations at a wide flow rate range, the same microfluidic system is re-structured to comprise four output channels. The particles collected from the output close to the side wall at lower flow rates can be collected from the other outputs at high flow rates since the focal line gets closer to the center with increasing flow rate. For example, 99.57% of the 9.9 μm diameter particles homogenously mixed in the fluid that is injected into the channel at 2.5 ml/min flow rate can be collected from the channel number two (FIG. 9 and FIG. 10).

Maintaining the focal quality in a wide flow rate range leads up to precise manipulation of the focal line of the particles inside the microchannel (1) by flow rate adjustment, and this enables enrichment of the particles at different working conditions by coming out from different outputs. At low flow rates, the particles are collected from the output close to the wall and at high flow rates the particles are collected from the other outputs close to the channel center.

Another advantage of the developed microchannel (1) is that it forces the particles or the cells to focus faster.

Figure 11:
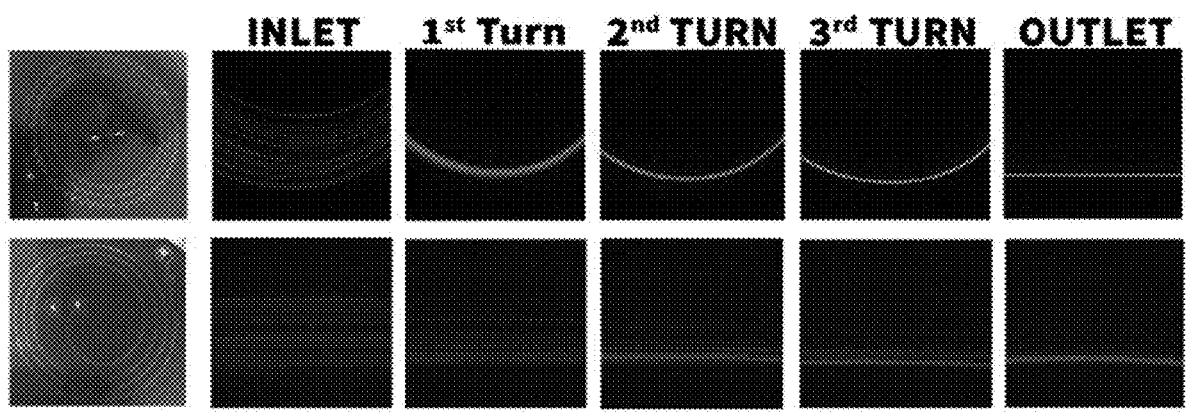
FIG. 11 is the microscope view of the particle focus formation speed comparison between the spiral microchannel geometry and the microchannel having a spiral geometry structured with asymmetrical curls.

In the conducted comparative experiments, while the 9.9 μm diameter particles complete focus formation at the second turn of the microchannel (1), a lower quality focus hardly forms at the fourth turn in spiral microchannel geometry (FIG. 11). This result shows that the developed microchannel (1) can perform the same job as the channel having spiral geometry while occupying less space.

Figure 12:
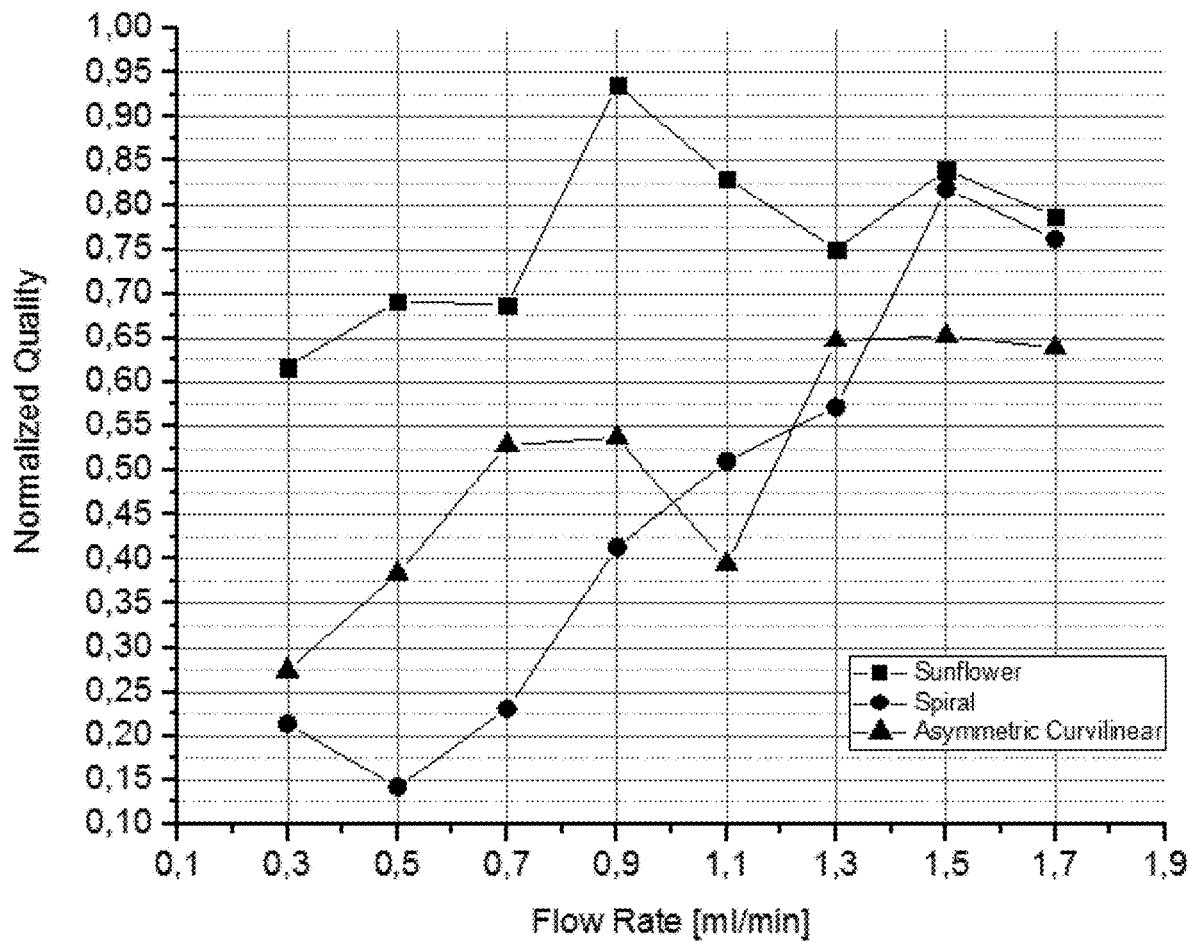
FIG. 12 is the graph of comparative experimental results obtained by mixing 9.9 μm diameter particles and the 3.0 μm diameter particles.

Lastly, in the experiments conducted with more than one particles, even a decrease in the quality of the focus formed by the microchannel (1) is observed, the quality of the collected particle focus is nevertheless better when compared to other systems. In the mixed particle experiments, while the 3.0 μm diameter red particles used along with the 9.9 μm diameter green particles are distributed inside the channel, the 9.9 μm diameter particles are focused close to the internal side wall of the channel. By this experiment, through integration of an output unit similar to the one shown in FIG. 9, it is shown that enrichment of particles with 9.9 μm diameters is possible. The flow rate values where best particle focal quality is obtained in other channel geometries match up with the optimum flow rate values obtained in other independent studies that can be found in the literature (FIG. 12).

What is claimed is:

1. A microchannel, comprising: asymmetrical curls; and the microchannel having a spiral geometry; wherein, the asymmetrical curls are positioned periodically on a spiral trajectory of the microchannel, and the microchannel is configured to enable a separation of metastatic cancer cells rarely present in blood from blood cells and enrichment thereof.

* * * * *